(12) United States Patent
Richardson et al.

(10) Patent No.: US 6,331,436 B1
(45) Date of Patent: Dec. 18, 2001

(54) TRACERS FOR HEAVY OIL

(75) Inventors: William C. Richardson, Bellaire, TX (US); Kevin D. Kimber, Riau (ID)

(73) Assignee: Texaco, Inc., White Plains, NY (US)

( * ) Notice: Subject to any disclaimer, the term of this patent is extended or adjusted under 35 U.S.C. 154(b) by 0 days.

(21) Appl. No.: 09/226,480

(22) Filed: Jan. 7, 1999

(51) Int. Cl.$^7$ .................................................. G01N 33/24

(52) U.S. Cl. ................................ 436/27; 436/29; 436/56; 436/60

(58) Field of Search .................................. 436/27, 29, 56, 436/60; 166/244.1, 270.2

(56) References Cited

U.S. PATENT DOCUMENTS

| | | | |
|---|---|---|---|
| 3,751,226 | * 8/1973 | Hesse et al. | 436/128 |
| 3,799,261 | * 3/1974 | Deans et al. | 137/1 |
| 3,902,362 | * 9/1975 | Tomich et al. | 166/250.01 |
| 4,058,366 | * 11/1977 | Cabbiness | 166/250.12 |
| 4,166,215 | 8/1979 | Anderson | 250/260 |
| 4,166,216 | 8/1979 | Cubberly, Jr. | 250/260 |
| 4,223,727 | 9/1980 | Sustek, Jr. et al. | 166/250 |
| 4,228,855 | 10/1980 | Sustek, Jr. et al. | 166/250 |
| 4,299,709 | 11/1981 | Carter et al. | 252/8.55 |
| 4,420,565 | * 12/1983 | Schmitt | 437/27 |
| 4,501,324 | * 2/1985 | Sandiford et al. | 166/250 |
| 4,520,109 | * 5/1985 | Simmonds et al. | 436/56 |
| 4,683,070 | 7/1987 | Munsell et al. | 242/33.4 |
| 4,742,873 | * 5/1988 | Craig | 166/252 |
| 4,755,469 | 7/1988 | Showalter et al. | 436/27 |
| 4,857,234 | 8/1989 | Gant et al. | 252/645 |
| 4,986,354 | 1/1991 | Cantu et al. | 166/279 |
| 5,111,882 | 5/1992 | Tang et al. | 166/252 |
| 5,246,860 | 9/1993 | Hutchins et al. | 436/27 |
| 5,498,596 | * 3/1996 | Ashjian et al. | 507/103 |

OTHER PUBLICATIONS

Encyclopedia of Chemical Technology, v. 5, Interscience, N.Y., 1950, p. 208.*

Stone, T., Perkins, E., and Schmidt, T., "Tracers in Analysis of Steamfloods," Paper No. 20, Third Technical Meeting of the South Saskatchewan Section, CIM, Regina, Canada, Sep. 1989.

Perkins, E.H., Young, B.K., Gunter, W.C., and Turner, J.C., "Evaluation of In–Situ Geochemical Tracers and Their Implication for Production at a South Midway Sunset Heavy Oil Reservoir," SPE#24946, presented at the SPE 67th Annual Technical Conf., Washington, DC, Oct. 4–7, 1992.

Skauge, A., Eleri, O.O., Graue, A., and Monstad, P., "Influence of Connate; Water on Oil Recovery by Gravity Drainage," SPE #27817, presented at the SPE/DOE Ninth Symposium on Improved Oil Recovery, Tulsa, OK., Apr. 17–20, 1994, pp. 381–389.

Graue, A., Kollveit, K., Lien, J.R., and Skauge, A., "Imaging Fluid Saturation Development in Long Coreflood Displacements," SPEFE, vol. 5, No. 4, Dec. 1990, pp. 406–412.

(List continued on next page.)

*Primary Examiner*—Jill Warden
*Assistant Examiner*—Yelena Gakh
(74) *Attorney, Agent, or Firm*—Morris N. Reinisch; Howrey Simon Arnold & White

(57) ABSTRACT

A process of using a non-radioactive tracer in the monitoring of the flow of a traced fluid is disclosed. The process includes injecting a tracer containing fluid at a first point and analyzing at least one sample from a second point in the flow of the fluid for the tracer compound. In one embodiment heavy oil is traced with a long chain hydrocarbon having a primary chain of more than 25 carbon atoms, the compound preferably being a saturated hydrocarbon. Exemplary tracer compounds include pentacosane ($C_{25}H_{52}$); hexacosane ($C_{26}H_{54}$), heptacosane ($C_{27}H_{56}$), octacosane($C_{28}H_{58}$), nonacosane($C_{29}H_{60}$), triacontane($C_{30}H_{62}$), hentriacontane ($C_3lH_{64}$), dotriacontane($C_{32}H_{66}$), tritriacontane ($C_{33}H_{68}$), tetratriacontane ($C_{34}H_{70}$) and the like.

12 Claims, 4 Drawing Sheets

OTHER PUBLICATIONS

Skauge, A., Aanonsen, S.I., and Graue, A., "Dynamic Fluid Saturation Profiles in the Analysis of Surfactant Flooding Core Displacement," SPE/DOE 17347, Sixth Symposium on Enhanced Oil Recovery, Tulsa, OK (Apr. 1988) pp. 289–302.

* cited by examiner

TRACERS FOR HEAVY OIL

BACKGROUND OF THE INVENTION

1. Field of the Invention

The present invention is generally directed to the use of organic compounds as tracers in monitoring the flow of fluids and in particular heavy oil. In one embodiment the flow of heavy oil in a subterranean formation is monitored and in another embodiment the flow of heavy oil through a tank and pipe system is monitored. In yet a third embodiment the flow of oil from different zones in a producing well may be monitored.

2. Background

Tracers are used in the petroleum industry in order to track fluid movement and monitor the changes in flow and composition in subterranean formations. The monitoring of the flow through a formation is particularly important in managing and maximizing production during thermal recovery operations. Tracers may be added to either the water/brine phase or the steam that is injected into the formation through an injection well. Examples include halide salts, boron salts, silicates, and other inorganic and organic water soluble salts. Oil soluble tracers may be injected as part of a "slug" of oil in an injection well. Examples of oil soluble tracers include oil soluble compounds of transition or rare earth metals or highly fluorescent compounds. The principle problem with the use of such compounds is that the technology used to detect the presence of these compounds in samples, (i.e. atomic absorption, atomic emission, ultrasensitive spectrofluorometry, Internally Coupled Plasma-Mass Spectroscopy (ICP-MS), etc.) is expensive, not suitable for field use and requires highly trained technicians.

Radio-isotopically labeled water soluble or oil soluble compounds have also been used a tracer compounds. These tracers are injected into the subterranean formation using an injection well in a similar manner as the corresponding non-radioactive tracers. The flow of oil in the subterranean formation is determined by monitoring samples taken from a production well and determining the concentration of radioisotope is determined in each sample. From such data, a time verses concentration curve provides information as to the flow characteristics of the subterranean formation. Examples of radio-isotopically labeled tracers include a $^{131}$I labeled iodoethanol, $^{59}$Fe labeled dicyclopentadienyl iron (II) (i.e. $^{59}$Fe-ferrocene) amongst others.

Although the use of radio-isotopically labeled tracers is very sensitive to low concentrations of the tracer in the sample, there are several problems with the use of these tracers. First is the handling and environmental concerns of using and detecting a radio-isotope. Often this requires specialized training and permits from governmental authorities. Cost is another concern since radio-isotopically labeled compounds are expensive and they are not typically recoverable from the produced fluids. Further, the injection of radio-isotopically labeled tracers "contaminates" the entire formation with a radio-isotope which alters the natural isotopic composition of the produced fluids. Such contamination may interfere with the scientific analysis of the produced fluid's characteristics. In particular, the use of radio-isotopically labeled tracers may interfere in the radio isotope dating of the formation. Finally, and not the least of importance, the use of a radio-isotope labeled tracer may be limited by the unduly short or excessively long half life of the radio-isotope.

Much of the work in tracer compounds for thermal recovery operations has focused on water or brine soluble tracers since such compounds can be easily added to the water, brine or steam injected into the formation during a water injection, steam flood, or other thermal recovery operations. Examples of such tracers may be found in U.S. Pat. No. 5,246,860 which discloses the use of carboxylic, and sulfonic acids and their salts as suitable tracers. Although oil soluble tracers are disclosed, they are limited to aniline and pyridine compounds that upon addition of acid form water soluble salts.

Despite the above developments in tracer technology, there exists a continuing need for oil soluble tracers, especially those that can be used in monitoring the flow of heavy oil during a steam flood or other thermal recovery process.

SUMMARY OF THE INVENTION

The present invention is generally directed to a process of monitoring the flow of a fluid from a first point to a second point, the first point being in fluid communication with the second point. The process includes injecting a fluid soluble tracer into the fluid to be traced at the first point and analyzing at least one sample from the second point for the tracer. The tracer may include a fluid soluble organic compound having more than 25 carbons that: is compatible with the characteristics of the fluid; is thermally and chemically stable under the conditions encountered between the first point and the second point and is present in a concentration such that it can be detected in the sample from the second point. It is preferred that the tracer be selected from long chain hydrocarbons having a primary chain of more that 25 carbon atoms, and more preferably that the tracer be a saturated hydrocarbon.

In one exemplary embodiment, the process may be used to monitor the flow of oil or other subterranean fluids in a subterranean formation. In another embodiment, the process may be used to monitor the flow of fluid through a system of tanks and pipes.

BRIEF DESCRIPTION OF THE DRAWINGS

These and other features of the present invention are more fully set forth in the following description of illustrative embodiments of the invention. The description is presented with reference to the accompanying drawings in which.

DESCRIPTION OF ILLUSTRATIVE EMBODIMENTS

The following terms and phrases are used herein and are intended to have the following meaning:

"traced fluid" means any fluid, (i.e. aqueous-based fluids (e.g. ground water, geothermal brines, fluids injected during steam floods, carbon dioxide floods, caustic floods, polymer floods, micellar-polymer floods and the like), and organic-based fluids (e.g. crude oil, natural gas and the like)) that may be traced with tracer compounds of the present invention;

"tracer compound" means a compound that is added to the traced fluid that has characteristics unique from the naturally occurring fluid such that the presence and quantity of the tracer can be determined.

"heavy oil" means oil having a API gravity less than about 25°. Such oils may be either naturally produced crude oil or refinery produced oil.

"primary chain" or "primary hydrocarbon chain" means the longest chain of carbon atoms that can be counted in the structure of the molecule. For example n-pentane, 2-methyl pentane, 3-methyl-2-pentene all have a five carbon primary chains.

The present invention is generally directed to the use of a non-radioactive tracer compound to track the flow of fluids. The tracer compounds of the present invention should have the following properties: 1) facile detection in small amounts, 2) no effect on the physical properties of the traced fluid, 3) minimal volatility at the temperatures encountered by the traced fluid, and 4) be available in bulk amounts at an economically viable cost.

Figure 1:
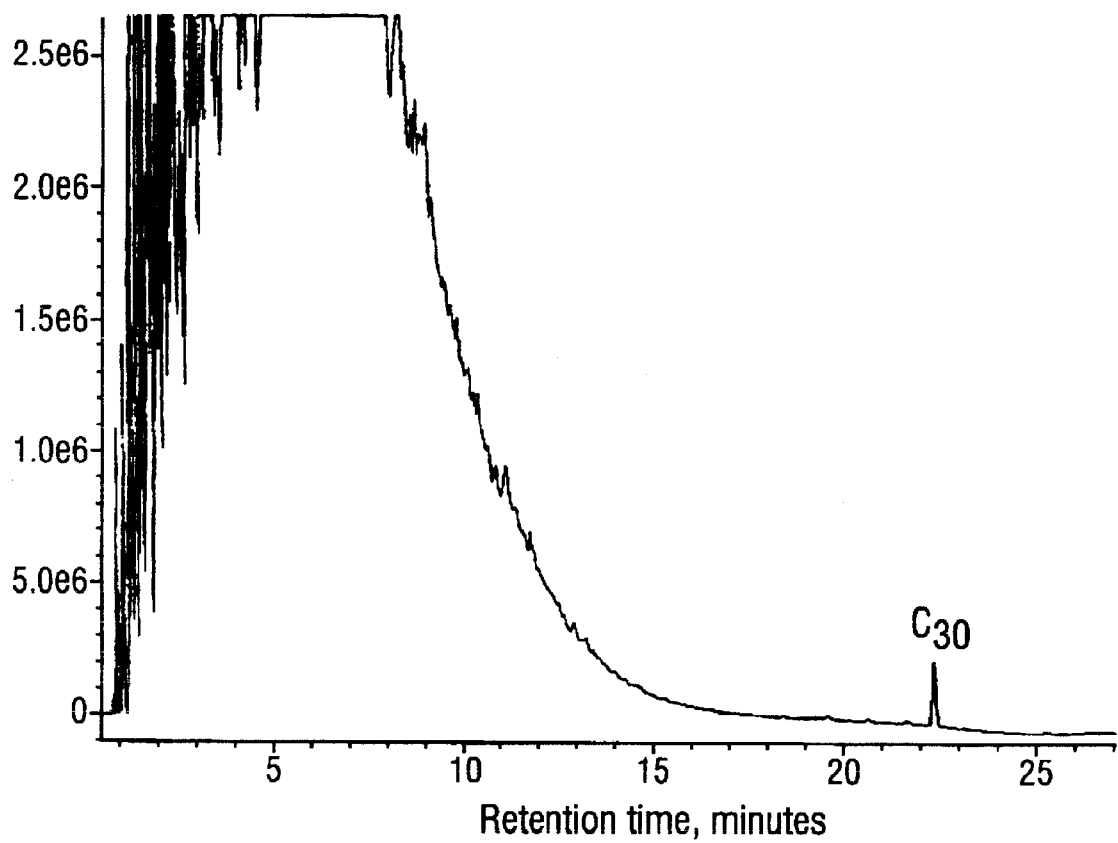
FIG. 1 is a graph of an exemplary gas chromatographic trace of retention time (x-axis) verses the relative response (y-axis) of a Kern River condensate including 300 ppm (w/w) of a tracer of the present invention.

Tracers of the present invention should be detectable in small amounts in the fluid to be traced. The present invention utilizes chromatography to detect the presence and concentration of the tracer in the traced fluid. A number of chromatography techniques can be used. For example, gas-liquid chromatography (GC), high pressure liquid chromatography (HPLC), column chromatography, thin layer chromatography (TLC), super-critical fluid chromatography (SCFC), and so forth may be used. All of these methods are known to be able to detect compounds in the part per million (ppm) range and in some cases parts per billion (ppb) reliably and quantitatively. Of critical importance in selecting a tracer to be detected by chromatography is its retention time versus that of the untraced sample. Ideally, the tracer will have a retention time that gives a unique peak in a portion of the chromatography trace that is otherwise approximately that of the baseline. That is to say the tracer should be detectable above the natural background content of the traced fluid. As an illustrative example, FIG. 1 shows a GC trace of a Kern River condensate including 300 ppm (w/w/) of a $C_{30}$ hydrocarbon tracer. The Y-axis represents the relative concentration while the X-axis represents time. Based on this data, one of skill in the art would note that the natural content of $C_{25}$+hydrocarbons are minimal. One of skill in the art should understand from this information that one could use gas-liquid chromatography and a $C_{30}$ hydrocarbon tracer in Kern River condensate. By keeping in mind the above selection criteria, compounds suitable for use in the present invention may be selected.

The determination of the concentration of any particular compound is possible by the use of standard concentration curves established with samples having a known concentration of the tracer compound. One of ordinary skill in the art should know how to prepare standard samples and derive a standard concentration curve. Once a standard concentration curve is established for a tracer compound in a particular type of traced liquid, the concentration of tracer compound in samples of the traced liquid with unknown amounts of compound can be determined. In addition, computer modeling software exists that can simulate the chromatography traces resulting from a complex mixture. Based on these simulations and comparison with the experimental chromatography trace, one can determine the concentration of the tracer compound in the sample given previously prepared known standards. Such techniques should be known to one skilled in the art of chromatography and in particular quantification of samples using chromatography.

As previously noted the tracer should be compatible with the characteristics of the traced fluid. That is to say, the tracer should not drastically alter the viscosity, pour point, molecular weight, metals content, volatility, or the final compositional utility of the traced fluid. In the above noted illustrative example, Kern River condensate was traced with a $C_{30}$ hydrocarbon. Such a tracer had a minimal affect on the viscosity, pour point, average molecular weight, and volatility of the traced fluid when compared to the untraced fluid. Because the tracer compound was a saturated long chain hydrocarbon (i.e. triacontane ($C_{30}H_{62}$) the addition of the tracer had no effect on the metals content or the final compositional utility of the Kern River condensate.

It is also important that the tracer have a minimal volatility under the temperature conditions encountered by the traced fluid. This characteristic is especially important in the monitoring the flow of heavy oil in subterranean formation during the course of a steam flood and other thermal recovery operation. One of skill in the art should understand that during the course of a steam injection operation, the subterranean formation will loose the volatile components of the heavy oil more rapidly that the less volatile components. Over time, a volatile tracer would be removed along with the naturally occurring volatile materials and the function of the tracer over the long term would be lost. Thus, in one illustrative embodiment of the present invention the tracer compound has a vaporization point preferably greater than 100° C. and more preferably greater that of the temperature of the steam injected. In another illustrative embodiment, the tracer compound has a vaporization point that is greater than the conditions encountered in the subterranean formation and more preferably has an atmospheric boiling point greater than 300° C. and preferably greater than 400° C. Compounds having such high boiling points ensure that the tracer compounds of the present invention remain with the heavy oil of the subterranean formation.

The tracer should also be thermally and chemically stable under the conditions encountered during the course of the tracing operation. A thermally stable tracer compound should not thermally decompose at the temperatures encountered by the flow of the traced fluid. Utilizing the above illustrative example, the tracer should be thermally and chemically stable under the conditions encountered in the subterranean formation. The tracer compound should be thermally stable (i.e. not appreciably decompose) under the temperatures generated during the steam flood recovery process which may be greater than 100° C. and often may greater than 150° C. The chemical stability of the tracer is also important because unwanted chemical reactions would reduce the usefulness of the tracer. Therefore the tracer should be selected so that it is compatible or chemically inert when mixed with the heavy oil to be traced.

Illustrative examples of suitable tracer compounds of the present invention are organic compounds selected from the long chain hydrocarbons in which the primary hydrocarbon chain has more than 25 carbon atoms. Aliphatic hydrocarbons are preferred and saturated hydrocarbons are more preferred. Examples of such compounds include, pentacosane ($C_{25}H_{52}$); hexacosane ($C_{26}H_{54}$), heptacosane ($C_{27}H_{56}$), octacosane($C_{28}H_{58}$), nonacosane($C_{29}H_{60}$), triacontane($C_{30}H_{62}$), hentriacontane($C_{31}H64$), dotriacontane ($C_{32}H_{66}$), tritriacontane ($C_{33}H_{68}$), tetratriacontane ($C_{34}H_{70}$) and the like. Mixtures of these compounds may also be used although single compounds are preferred. In the embodiment shown above, triacontane is used as a tracer for Kern River condensate.

One of ordinary skill in the art should realize that because of the different retention times, different tracers can be used in different wells to monitor the flow of oil from an injection well to the producing well. For example, in one well a pentacosane tracer could be injected and in a second injection well a triacontane could be injected. The presence or absence of either compound and its relative concentration in the samples taken from the producing well may provide useful information about the flow of oil from each well. Thus with such information the injection of steam in one or the other well can be adjusted so as to give a more uniform production of heavy oil from the formation.

In one illustrative embodiment, the flow of a subterranean fluid in a subterranean formation is monitored. The process includes injecting a tracer compound containing fluid into at least one injection well which would be in fluid communication with the subterranean formation. At least one sample should be taken from at least one producing well that itself will be in fluid communication with the subterranean formation. Preferably, multiple samples will be taken over time and the concentration of the tracer may be determined as a function of time. This data could then be used to determine the time dependent flow characteristics of the subterranean formation. It also could be used to determine the optimum fluid injection and fluid production rates for the subterranean formation. Such information would be especially helpful when managing the thermal recovery of oil using injected steam or other recovery techniques.

Another illustrative embodiment of the present invention is a process for monitoring the flow of oil from a first point in a subterranean formation to a second point in the subterranean formation. The illustrative process would include injecting a tracer containing fluid into an injection well and subsequently injecting the tracer containing fluid into the formation. The tracer may be an oil soluble organic compound having more than 25 carbons and preferably a long chain hydrocarbon having a primary chain of more that 25 carbons and even more preferably the tracer may be a saturated hydrocarbon. The oil soluble tracer compound should preferentially dissolve and distribute itself in the oil present in the formation. Thus as traced oil in the subterranean formation is produced from the second point in the formation, the concentration of the tracer could be monitored over time. Such data may provide the field operator a better idea of the state of the formation and the effectiveness of the recovery operation.

In yet a third illustrative embodiment, the tracer of the present invention could be used to monitor the flow and residency of oil from a first point to a second point in a complex system of storage tanks and pipes. Such an embodiment may be especially useful in tracking the flow of oil and heavy oil through refinery processes and in monitoring the effectiveness of mixing and blending operations. The process of the present illustrative embodiment would include the injection of the oil soluble tracer into the in-flowing oil stream at a known concentration. This could be done as a slug (i.e. a portion of oil with a high concentration of tracer) or the tracer could be metered into the in-flowing oil stream at a constant concentration. As the traced oil flows through the tank and pipe system the traced oil should mix with untraced oil that is present in the tank. When such mixing occurs, the concentration of the tracer decreases. Samples of the oil in the tanks and in the pipes may be taken from check valves and other sampling ports along the flow path. The concentration of the tracer could be determined and the flow characteristics of the system could be determined. In this manner "dead spots" in which no mixing of oil occurs could be detected and eliminated. Another application of the present invention may be to monitor the overall residency time of the oil in the system or in any particular part of the system. In such a test a slug of tracer compound could be introduced into the in-flowing stream of oil at a first point in the system. At least one sample could be taken from a second point after a predetermined period of time and the concentration of the tracer in the sample determined. When multiple samples are taken from differing locations in the stream, flow parameters such as the residency time of the traced oil, the flow rate and the extent of mixing could be determined by monitoring several points over time. Such information may be useful in the designing and monitoring of oil treatment systems and other refinery systems. In one embodiment the tracer may be an oil soluble compound having more than 25 carbon atoms. Preferably the tracer may be a long chain hydrocarbon in which the primary chain has more than 25 carbon atoms and more preferably the tracer may be a saturated hydrocarbon.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

General Experimental Information

The tracer material selected and utilized in the following examples was the saturated aliphatic hydrocarbon, triacontane ($C_{30}H_{62}$) which is commercially available in high purity from chemical suppliers. The calculated atmospheric boiling point is about 650° C.

Solution mixing was accomplished using one of three different techniques at two temperatures. Small sample (<100 ml) solutions were mixed by either hand shaking at room temperature, hand shaking at elevated temperature (<48° C.), or by mechanical wrist shaker at room temperature. Large sample solutions of oil and tracer were mixed by a mechanical stirrer either at room temperature or elevated temperature.

Standard solutions having known concentration were prepared by dilution of a primary standard solution into which the tracer concentration was 10,000 ppm in Kern River condensate. Kern River condensate is a clear, slightly colored hydrocarbon fluid. Other similar mixtures of hydrocarbons may be used as should be apparent to one of skill in the art.

Gas-Liquid Chromatography (GC) analysis of the samples was carried out on conventional gas chromatograph with a flame ionization detector (FID) and a 60 meter DB-1 Megabore open tubular column coated with 1.5 microns of a methylpolysiloxane liquid phase. Helium gas was used as the carrier gas phase. Temperature and flow parameters were adjusted within the range of appropriate values so as to give optimum resolution of the peaks of interest.

In some cases the viscosity of the sample was reduced by dilution into carbon disulfide. Carbon disulfide was selected as the preferred diluent because it does not give an appreciable response from the flame ionization detector. Other suitable diluents may be used and will be known to one of skill in the art. Each sample to be diluted was carefully weighed and then a known amount of diluent was added. The mixture was hand shaken until homogeneous. The sample was then analyzed by liquid-gas chromatography.

Peak area integration was made of individual tracer peaks to enhance accuracy and to quantitate the amount of tracer in the sample. Peak isolation software was used to draw in the background base line from which peak integration was conducted. Mathematical adjustments for dilution of the sample were conducted if needed. One of skill in the art should readily understand and appreciate the need for the above techniques and processes in order to achieve the consistent and accurate results of the present invention.

EXAMPLE 1

Triacontane was diluted into Kern River condensate samples so as to give known values of concentration. Kern River Condensate is an exemplary oil having a density of 0.8602 g/ml, an API gravity of 33.0°, and a viscosity of 80 centipoise at 72° F. GC analysis shows that triacontane has a retention time in the range of 22.3 to 22.4 min. when the flow of carrier gas was about 37 cm3/min. An exemplary GC trace of a sample containing 300 ppm (w/w) of triacontane in Kern River condensate is shown in FIG. 1. Upon review of this figure, one of skill in the art should appreciate that triacontane can function as a tracer compound for Kern River condensate. To obtain a calibration curve, samples of Kern River condensate containing known amounts of triacontane were analyzed by GC and the integrated peak area for triacontane was determined. The following table (Table 1) gives exemplary data.

TABLE 1

| Solution | Gravimetric Tracer Conc. (ppm, w/w) | Integrated Peak Area | Predicted Tracer Conc. (ppm) | Δ (ppm)* |
|---|---|---|---|---|
| Condensate | 0 | 0 | −2.73 | 2.73 |
| 2766-11 A | 212 | 346,271 | 214.7 | −2.70 |
| 2766-11 A | 212 | 345,284 | 214.1 | −2.08 |
| 2766-11 C | 356 | 567,468 | 353.6 | 2.40 |
| 2766-11 C | 356 | 579,248 | 361.0 | −5.00 |
| 2766-11 C | 356 | 564,790 | 351.9 | 4.08 |
| 2766-11 D | 852 | 1,360,242 | 851.4 | 0.57 |

*Δ (ppm) = (predicted tracer conc.) − (Gravimetric Tracer Conc.)

Figure 2:
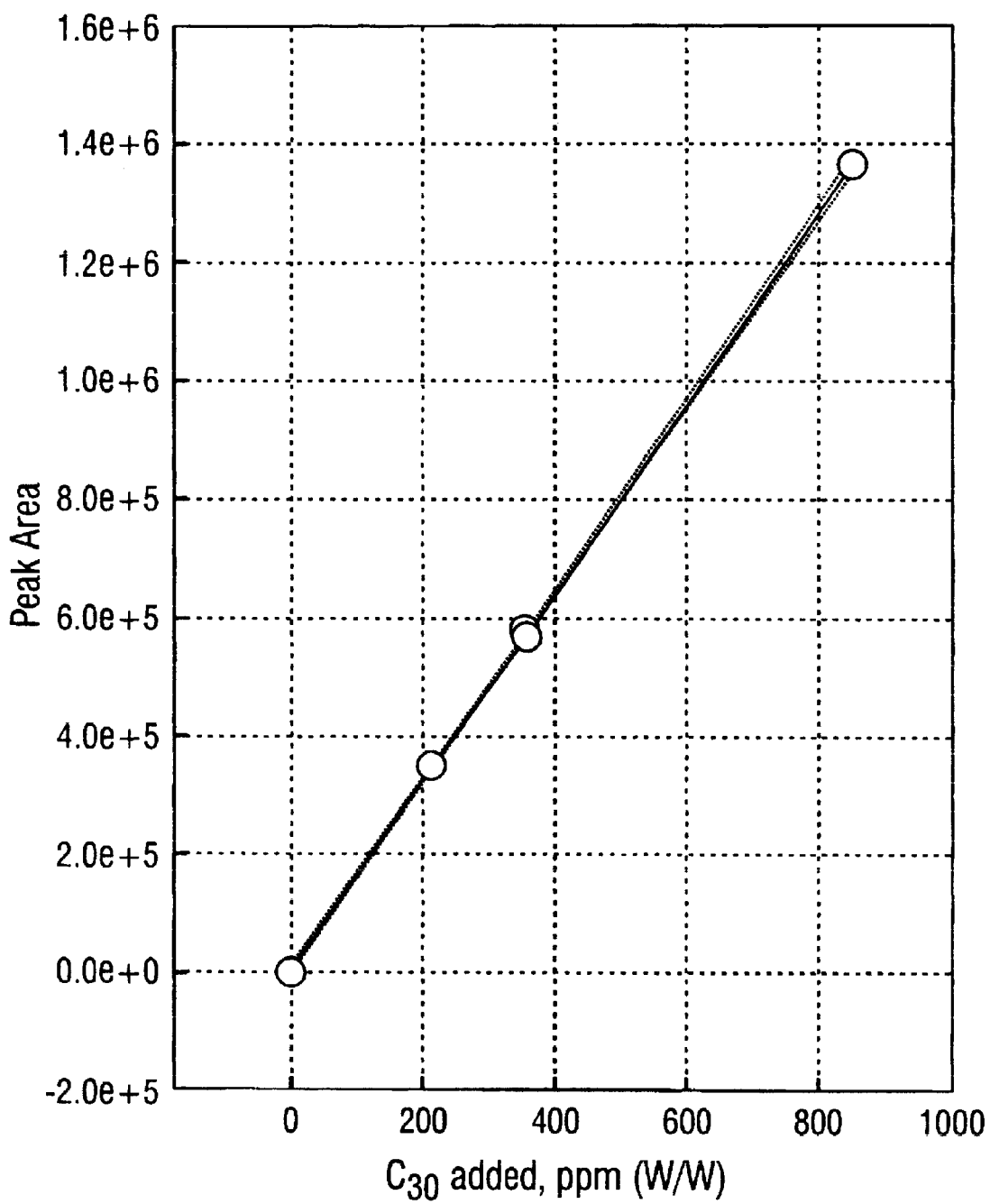
FIG. 2 is a calibration curve of a tracer of the present invention in Kern River condensate including the least squares 95% confidence interval.

The known values of tracer concentration (x-axis) and the integrated peak area (y-axis) were fit into a linear least squares equation of the form $$PA = m[ppm] + b$$

wherein PA is the integrated peak area for the tracer, ppm is the known concentration of the sample, m is the slope of the linear least squares line and B is the y intercept. In the present example, the value of m=1592 and the value of b=4359 and a correlation coefficient of 0.9998 was found. FIG. 2 shows the above linear fit.

Using the least squares fit as a concentration calibration curve, the GC-determined values for the triacontane concentration were predicted for each of the samples based on the integrated peak area. (See Column 4, Table 1). The difference in the more accurate gravimetric concentration of tracer and the predicted tracer concentrations are given in Column 5, Table 1. The standard deviation error in the calibration curve was calculated to be about 3.1 ppm.

Given the above data, one of skill in the art should be able to determine not only the presence but also the concentration of the triacontane tracer compound in unknown samples of Kern River Condensate.

EXAMPLE 2

Triacontane was diluted into Kern River Station 36 oil samples so as to give known values of concentration. Kern River Station 36 heavy oil is an exemplary heavy oil having a density of 0.972 g/ml, an API gravity of 13.0°, and a viscosity of 10,000 centipoise at 72° F. Because of the high viscosity of the Kern River Station 36 oil, samples for GC analysis were diluted with carbon disulfide as previously noted. GC analysis shows that triacontane has a retention time in the range of 22.3 to 22.4 min. when the flow of carrier gas was about 37 cm$^3$/min.

To obtain a calibration curve, samples of Kern River Station 36 oil containing known amounts of triacontane were analyzed by GC and the integrated peak area for triacontane was determined. The following table (Table 2) gives exemplary data.

TABLE 2

| Solution | Gravimetric Tracer Conc. (ppm, w/w) | Integrated Peak Area | Predicted Tracer Conc. (ppm) | Δ (ppm)* |
|---|---|---|---|---|
| 2766-6 J | 0 | 828,889 | 65.4 | −65.4 |
| 2766-11 F | 98.6 | 833,973 | 68.4 | 30.2 |
| 2766-11 F | 98.6 | 877,223 | 94 | 4.64 |
| 2766-11 G | 305 | 1,208,730 | 290 | 15 |
| 2766-11 E | 612 | 1,642,150 | 546 | 65.6 |
| 2766-11 H | 726 | 1,976,675 | 739 | −12.9 |
| 2766-11 B | 1044 | 2,546,177 | 1081 | −37.1 |

*Δ (ppm) = (predicted tracer conc.) − (Gravimetric Tracer Conc.)

Figure 3:
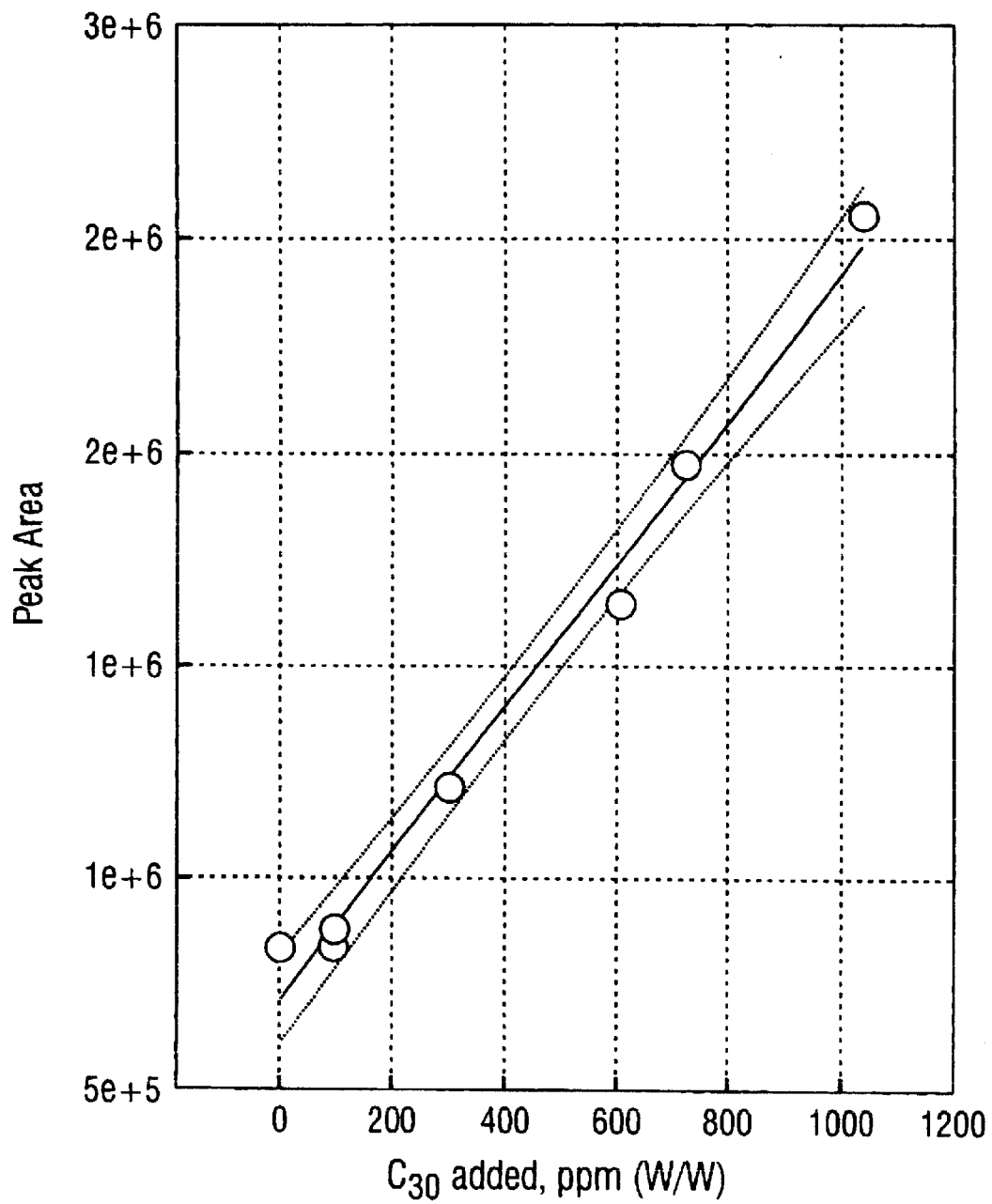
FIG. 3 is a calibration curve of a tracer of the present invention in Kern River heavy oil including the least squares 95% confidence interval.

The known values of tracer concentration (x-axis) and the integrated peak area (y-axis) were fit into a linear least squares equation of the form $$PA = m[ppm] + b$$

wherein PA is the integrated peak area for the tracer, ppm is the known concentration of the sample, m is the slope of the linear least squares line and B is the y intercept. In the present example, a good linear correlation ($r^2$=0.9878) was achieved with the value of m=1690 and the value of b=718, 374. The results of the linear regression are shown in FIG. 3

Using the least squares fit as a concentration calibration curve, the GC determined values for the triacontane concentration were predicted for each of the samples based on the integrated peak area. (See Column 4, Table 2). The difference in the more accurate gravimetric concentration of tracer and the predicted tracer concentrations are given in Column 5, Table 2. The standard deviation error in the calibration curve was calculated to be about 40.1 ppm. One of skill in the art would understand that the standard deviation value could be lowered by the use of peak modeling techniques, based on standard samples.

Given the above data, one of skill in the art should be able to determine not only the presence but also the concentration of the triacontane tracer compound in unknown samples of Kern River Station 36 oil and other exemplary heavy oils.

EXAMPLE 3

Triacontane was diluted into Kern River AWT #6 oil samples so as to give known values of concentration. Kern River AWT #6 heavy oil is an exemplary heavy oil having a density of 0.9820 g/ml, an API gravity of 12.6°, and a viscosity of 9,000 centipoise at 72° F. Because of the high viscosity of the oil, samples for GC analysis were diluted with carbon disulfide as previously noted. GC analysis shows that triacontane has a retention time in the range of 22.3 to 22.4 min. when the flow of carrier gas was about 37 cm³/min.

To obtain a calibration curve, samples of Kern River AWT #6 oil containing known amounts of triacontane were analyzed by GC and the integrated peak area for triacontane was determined. The following table (Table 3) gives exemplary data.

TABLE 3

| Solution | Gravimetric Tracer Conc. (ppm, w/w) | Integrated Peak Area | Predicted Tracer Conc. (ppm) | Δ (ppm)* |
|---|---|---|---|---|
| 2766-21 D | 0 | 976,104 | 22.2 | -22.2 |
| 2766-21 D | 0 | 935,052 | 10.3 | -10.3 |
| 2766-21 B | 118 | 1,331,876 | 125 | -7.29 |
| 2766-21 A | 499 | 2,353,085 | 421 | 77.9 |
| 2766-21 A | 499 | 2,663,807 | 511 | -12.1 |
| 2766-21 C | 1232 | 5,103,891 | 1271 | 14.1 |
| 2766-21 C | 1232 | 5,291,188 | 1272 | -40.1 |
| 2766-21 E | 1000 | 4,446,433 | 1014 | 14.0 |
| 2766-11 F | 1000 | 4,397,418 | 1028 | 28.0 |

*Δ (ppm) = (predictedtracer conc.) − (Gravimetric Tracer Conc.)

Figure 4:
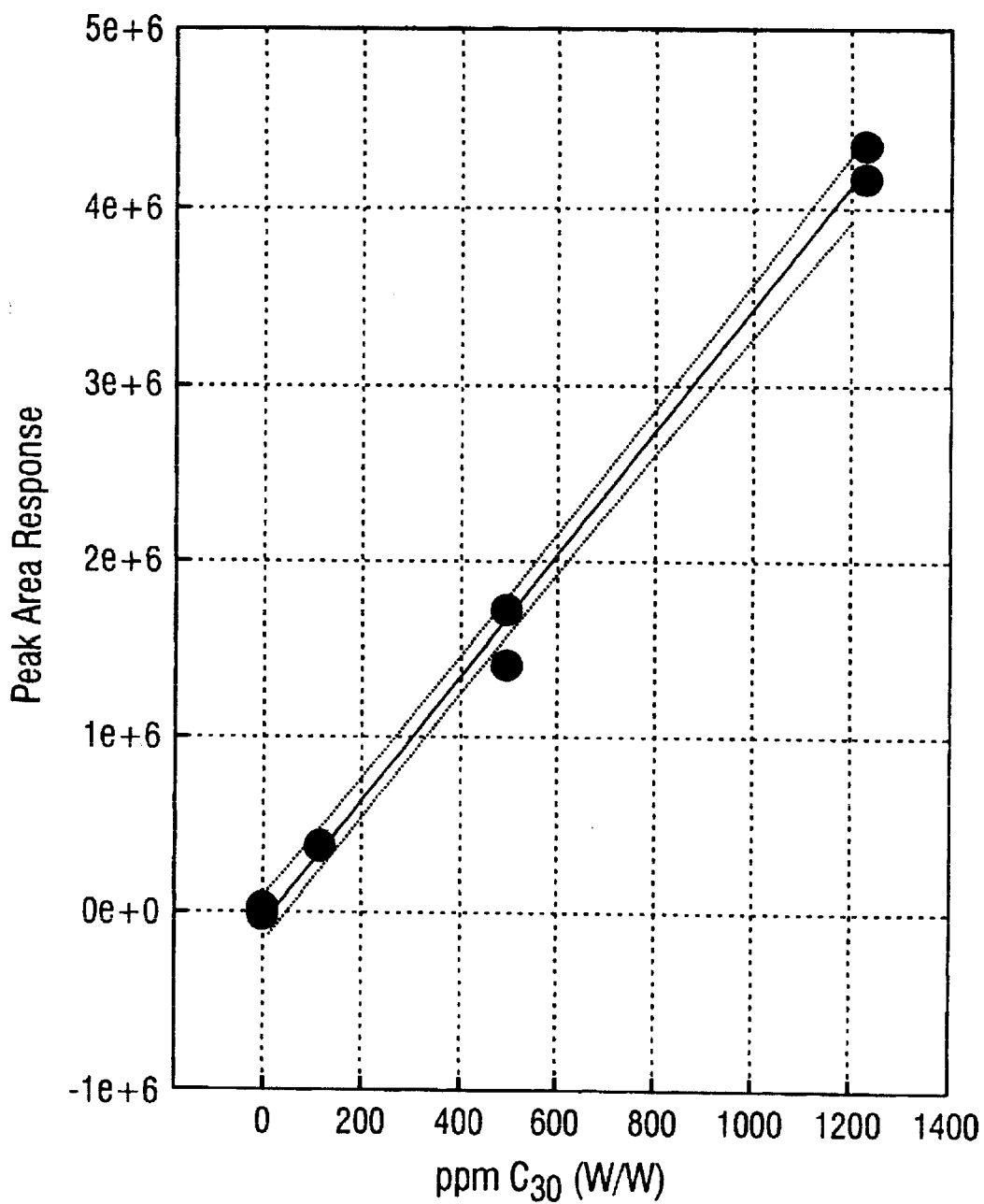
FIG. 4 is a calibration curve of a tracer of the present invention in Kern River AWT #6 heavy oil including the least squares 95% confidence interval.

The known values of tracer concentration (x-axis) and the integrated peak area (y-axis) were fit into a linear least squares equation of the form $$PA = m[ppm] + b$$

wherein PA is the integrated peak area for the tracer, ppm is the known concentration of the sample, m is the slope of the linear least squares line and B is the y intercept. In the present example, a good linear correlation ($r^2 = 0.9950$) was achieved with the value of m=3452 and the value of b=899, 335. The results of the linear regression are shown in FIG. 4

Using the least squares fit as a concentration calibration curve, the GC determined values for the triacontane concentration were predicted for each of the samples based on the integrated peak area. (See Column 4, Table 3). The difference in the more accurate gravimetric concentration of tracer and the predicted tracer concentrations are given in Column 5, Table 3. The standard deviation error in the calibration curve was calculated to be about 35.2 ppm. One of skill in the art would understand that the standard deviation value could be lowered by the use of peak modeling techniques, based on standard samples.

Given the above data, one of skill in the art should be able to determine not only the presence but also the concentration of the triacontane tracer compound in unknown samples of Kern River AWT#6 oil and other exemplary heavy oils.

While the compositions and methods of this invention have been described in terms of preferred embodiments, it will be apparent to those of skill in the art that variations may be applied to the process described herein without departing from the concept, spirit and scope of the invention. All such similar substitutes and modifications apparent to those skilled in the art are deemed to be within the spirit, scope and concept of the invention as it is set out in the following claims.

What is claimed is:

1. A process for monitoring the flow of a traced fluid in a subterranean formation, the process comprising:

injecting a tracer containing fluid into at least one injection well, said well being in fluid communication wit the subterranean formation; and analyzing at least one sample from at least one producing source, said producing source being in fluid communication with the subterranean formation, wherein the term comprises an organic compound having more than 25 carbons that: is at least patally soluble in the traced fluid; is compatible with the characteristics of the thawed fluid; is involatile upon the injection of steam into the subterranean formation; is thermally and chemically stable under the conditions encountered in the subterranean formation and has a negligible effect on metals content.

2. A process for monitoring the flow of a traced fluid in a subterranean formation, the process comprising:

injecting a tracer containing fluid into at least one injection well, said well being in fluid communication with the subterranean formation; and analyzing at least one sample from at least one producing source, said producing source being in fluid communication with the subterranean formation, wherein the tracer comprises an organic compound having more than 25 carbons that; is at least partially soluble in the traced fluid; is compatible with the characteristics of the traced fluid; is involatile upon the injection of steam into the subterranean formation; is thermally and chemically stable under the conditions encountered in the subterranean formation and wherein the tracer is an organic compound selected from long chain hydrocarbons having a primary chain of more than 25 carbon atoms and has a negligible effect on trace metals content of the traced fluid.

3. The process of claim 2 wherein the tracer is a saturated hydrocarbon.

4. The process of claim 3 wherein the tracer is triacontane.

5. A process for monitoring the flow of oil from a first point in a subterranean formation to a second point in a subterranean formation, the process comprising:

injecting a tracer containing fluid into at least a first well, said first well being in fluid communication with the first point in the subterranean formation;

analyzing at least one sample from at least a second well, said second well being in fluid communication with the second point in the subterranean formation wherein the tracer comprises an oil soluble organic compound having more than 25 carbons that: is compatible with the characteristics of the subterranean oil; is involatile upon the injection of steam into the subterranean formation; is thermally and chemically stable under the conditions encountered in the subterranean formation, has no effect upon the metals content of the oil, and is present in a concentration such that it can be detected in the sample from the producing well.

6. A process for monitoring the flow of oil from a first point in a subterranean formation to a second point in a subterranean formation, the process comprising:

injecting a tracer containing fluid into at least a first well, said first well being in fluid communication with the first point in the subterranean formation;

analyzing at least one sample from at least a second well, said second well being in fluid communication with the second point in the subterranean formation wherein the tracer comprises an oil soluble organic compound having more than 25 carbons that: is compatible with the characteristics of the subterranean oil; is involatile upon the injection of steam into the subterranean formation; is thermally and chemically stable under the conditions encountered in the subterranean formation and is present in a concentration such that it can be detected in the sample from the producing well and wherein the tracer is an organic compound selected from long chain hydrocarbons having a primary chain of more that 25 carbon atoms and has a negligible effect on trace metals content of the traced fluid.

7. The process of claim 6 wherein the tracer is a saturated hydrocarbon.

8. The process of claim 7 wherein the tracer is triacontane.

9. A process of monitoring the flow of an oil from a first point to a second point, the first point being in fluid communication with the second point, the process comprising:

injecting a oil soluble tracer into the oil at the first point and analyzing at least one sample from the second point for the tracer wherein the tracer comprises an oil soluble organic compound having more than 25 carbons that: is compatible with the characteristics of the oil; is thermally and chemically stable under the conditions encountered between the first point and the second point, has no impact on the metals content of the oil, and is present in a concentration such that it can be detected in the sample from the second point.

10. A process of monitoring the flow of an oil from a first point to a second point, the first point being in fluid communication with the second point, the process comprising:

injecting a oil soluble tracer into the oil at the first point and analyzing at least one sample from the second point for the tracer wherein the tracer comprises an oil soluble organic compound having more than 25 carbons that: is compatible with the characteristics of the oil; is thermally and chemically stable under the conditions encountered between the first point and the second point and is present in a concentration such that it can be detected in the sample from the second point and wherein the tracer is selected from long chain hydrocarbons having a primary chain of more that 25 carbon atoms and has a negligible effect in trace metals content of the traced fluid.

11. The process of claim 10 wherein the tracer is a saturated hydrocarbon.

12. The process of claim 11 wherein the tracer is triacontane.

* * * * *